United States Patent [19]

Liao

[11] 4,284,354
[45] Aug. 18, 1981

[54] SENSITIVE NONLINEAR OPTICAL SPECTROSCOPY

[75] Inventor: Paul F. Liao, Fair Haven, N.J.

[73] Assignee: Bell Telephone Laboratories, Incorporated, Murray Hill, N.J.

[21] Appl. No.: 87,877

[22] Filed: Oct. 24, 1979

[51] Int. Cl.³ .............................................. G01J 3/44
[52] U.S. Cl. ..................................... 356/301; 356/318
[58] Field of Search ................ 356/301, 307, 317, 318

[56] References Cited

U.S. PATENT DOCUMENTS 4,193,690  3/1980  Levenson et al. .................... 356/301

FOREIGN PATENT DOCUMENTS 46-7913  2/1971  Japan ........................................ 356/301

OTHER PUBLICATIONS

Moore et al., *Analytical Chemistry*, vol. 45, No. 12, Oct. 1973, pp. 2009–2014.

Eesley et al., *Digest of Technical Papers*, Jun. 1977, pp. 31 and 32.
Levenson, *Physics Today*, May 1977, pp. 44–47.
Sorem et al., *Optical Communications*, vol. 5, No. 3, Jun. 1972, pp. 148–151.
Moses et al., *Optics Letters*, vol. 1, No. 4, Oct. 1977, pp. 115–117.

*Primary Examiner*—F. L. Evans
*Attorney, Agent, or Firm*—Michael B. Einschlag

[57] ABSTRACT

Saturation spectroscopy involving synchronous phase-sensitive detection and measurement of the intensity of the output when one of the input beams is chopped has a drawback that scattered light and fluorescence from the sample will also be chopped and produce a large background signal. According to the present invention, the direction of propagation of one of the input beams is modulated. This causes the direction of propagation of the output to be similarly modulated while producing only a negligible effect on the background radiation from scattering and fluorescence.

8 Claims, 3 Drawing Figures

SENSITIVE NONLINEAR OPTICAL SPECTROSCOPY

BACKGROUND OF THE INVENTION

This invention pertains to the field of spectroscopy and more specifically to nonlinear spectroscopy.

Nonlinear spectroscopy with laser sources can be performed with high resolution and high sensitivity. Nonlinear spectroscopic techniques take advantage of the nonlinearity of the medium under study. The nonlinearity is greatly enhanced at natural resonances and this property is used to detect resonances. This involves subjecting the medium to several input beams and measuring the intensity of the output beams as a function of the frequencies of the input beams. The sensitivity of nonlinear spectroscopy is often limited by background light due to fluorescence and scattering. One scheme to reduce the effects of background is described in an article entitled "Saturation Spectroscopy in Molecular Iodine by Intermodulated Fluorescence" by M. S. Sorem and A. L. Schawlow, *Optics Communications*, Vol. 5, No. 3, June 1972, pp. 148–151 involves synchronous phase-sensitive detection and measurement of the intensity of the output when the input beams are chopped at two different frequencies. The phase-sensitive detection must be made at the sum frequency. If one detects at the fundamental modulation frequencies a large background signal is observed because the scattered light and fluorescence from the sample will be modulated at those frequencies.

SUMMARY OF THE INVENTION

The present invention pertains to a method and apparatus for sensitive nonlinear spectroscopy.

The interaction in which several excitation beams are mixed together by a nonlinear medium to produce an output beam is maximized when the frequencies of the excitation beams, or the appropriate sums or differences thereof, are tuned to a resonance in the nonlinear medium and the interaction is phasematched. According to the present invention, the direction of propagation of at least one of the excitation beams is modulated. This causes the direction of propagation of the output beam to be similarly modulated while producing only a negligible effect on the background radiation from scattering and fluorescence. The modulated output beam is then detected and that part of the signal which is synchronous with the modulation is used to provide for high sensitivity by elimination of the background.

BRIEF DESCRIPTION OF THE DRAWING

A complete understanding of the present invention may be gained from a consideration of the following detailed description presented hereinbelow in connection with the accompanying drawings in which.

DETAILED DESCRIPTION

Figure 1:
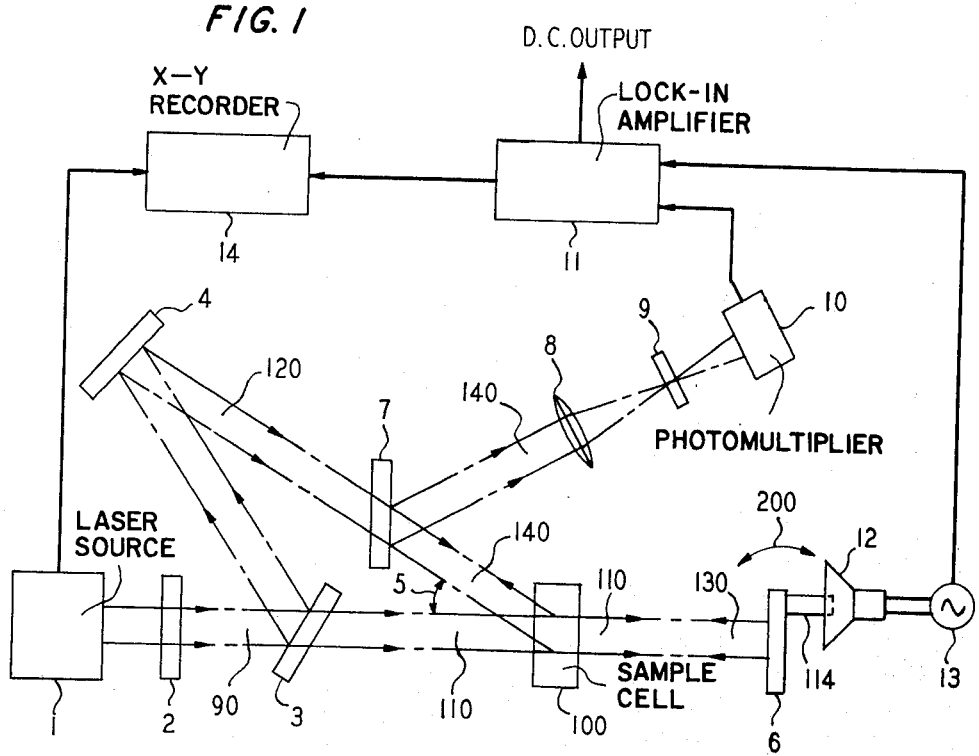
FIG. 1 shows a diagram of an embodiment of the present invention using four-wave degenerate mixing spectroscopy on a sodium vapor.

FIG. 1 shows an embodiment of the present invention which is used to perform a spectroscopic analysis. The material inside cell 100 may be an atomic or a molecular vapor. In the present embodiment the material inside cell 100 is a sodium vapor. The embodiment shown in FIG. 1 utilizes the physical phenomenon of degenerate four-wave mixing, with the vapor in cell 100 as a nonlinear medium, to provide generation of time reversed (phase-conjugated) wavefronts. Efficient generation is obtained by utilizing the large nonlinearity associated with the saturated absorption of narrow resonances in the vapor. In vapors the generation efficiency versus the excitation wavelength at low power levels exhibits a narrow Doppler-free lineshape in spite of the effects of atomic motion and hence, degenerate four-wave mixing provides an excellent method for high resolution spectroscopy.

Tunable laser radiation is provided by laser source 1. In a study of atomic sodium vapor I have used tunable laser radiation from an actively-stabilized single-mode cw dye laser, Coherent Model 599, which is pumped by an argon ion laser. The dye laser output was passed through circular polarizer 2 to provide optical isolation. Because I used circularly polarized light, optical pumping of the atomic sodium vapor in cell 100 caused only the $3S_{\frac{1}{2}}$ (F=2)→$3P_{3/2}$ (F=3) and $3S_{\frac{1}{2}}$ (F=1)→$3P_{3/2}$ (F=0) transitions to produce significant signals. A 50 percent beam splitter 3 and mirror 4 were used to divide laser bean 90 into pump bean 110 and object beam 120. Pump beam 110 and object beam 120 were incident upon cell 100 at angle 5 with respect to each other. Mirror 6 provided counterpropagating beam 130 when pump beam 110 impinged thereon after passing through cell 100. cell 100 was 1 mm thick and the effective sodium density was maintained at $3.6\times10^{11}$ cm$^{-3}$ by a side arm oven, not shown, while the main cell temperature was 215° C. For this study I defined the density of the sodium atoms to be the density of atoms in the $3S_{\frac{1}{2}}$ (F=2, $m_p$=2) state. This is the only state which will interact with the circularly polarized laser light once optical pumping has occurred. (The optical pumping is complete within a few hundred nsec.)

The critical aspect of the present invention involves a slight modulation of the direction of beam 130. This was achieved by a modulation of the angular orientation of mirror 6 as shown in FIG. 1 by arrow 200. As a result of this directional modulation, the phasematching conditions for four-wave degenerate mixing are changed and the direction in which the time-reversed beam 140 is emitted is slightly modulated. The emitted wave 140 is picked off by beam splitter 7 and focused with lens 8 through a $5\times10^{-3}$ cm diameter pinhole 9 and detected with photomultiplier 10. When the orientation of mirror 6 is driven in a sinusoidal fashion at a 1 kHz rate, the signal intensity which passes through pinhole 9 is also modulated. An angular modulation having a maximum deviation of 0.5 milliradians produces a 100 percent modulation of the signal. Because this angular modulation is so small, the scattered light and fluorescence intensity are unaffected; only the desired signal is modulated. Therefore, provided the residual background which passes through the pinhole is not large enough to saturate the detector, the conjugate wave is readily detected with lock-in amplifier 11. The lock-in amplifier 11 converts only that part of the input signal from detector 10 that is synchronous with the modulation signal provided by voltage source 13 into a d.c. level, which level is proportional to the desired signal. The remaining portions of the signal are not synchronous and remain as a. c. components which are removed by low-pass filters. X-Y recorder 14 was used to record the input signal and detected output signal. With this technique we have detected signals $10^9$ smaller than the incident pump and object intensities. It should be clear to those skilled in the art as to how this directional modulation could be performed. For example, I affixed rod 114 both to mirror 6 and radio speaker 12. Voltage source 13 caused speaker 12 to oscillate and induce the desired angular modulation of mirror 6.

Figure 2:
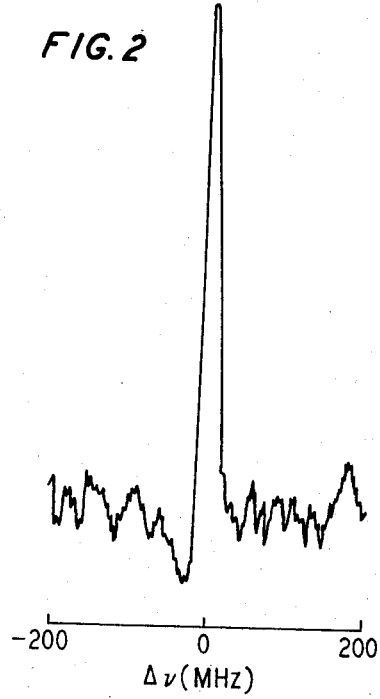
FIG. 2 shows a graph of conjugate wave intensity versus laser frequency for an angle of 22 degrees between the pump and object beams.

FIG. 2 shows the measured lineshape for conjugate wave generation versus excitation frequency in the limit of low intensity. The pump intensity was 6 mW/cm$^2$, the object intensity was 3 mW/cm$^2$, angle 5 shown in FIG. 1 was 22°, and each beam was collimated and had a 4 mm diameter. The Doppler-free character of the lineshape is due to the requirement that the atoms be simultaneously resonant with counterpropagating beams.

I found that the line-width of output beam 140 was independent of variations in angle 5 while the intensity of the time-reversed signal decreased as [sin (angle 5)]$^{-2}$.

The results described hereinabove demonstrate that degenerate four-wave mixing provides an excellent tool for spectroscopic copic analysis and that the modulation technique with respect to the counterpropagating beam allows excellent discrimination from any residual background due to fluorescence and scattering.

Figure 3:
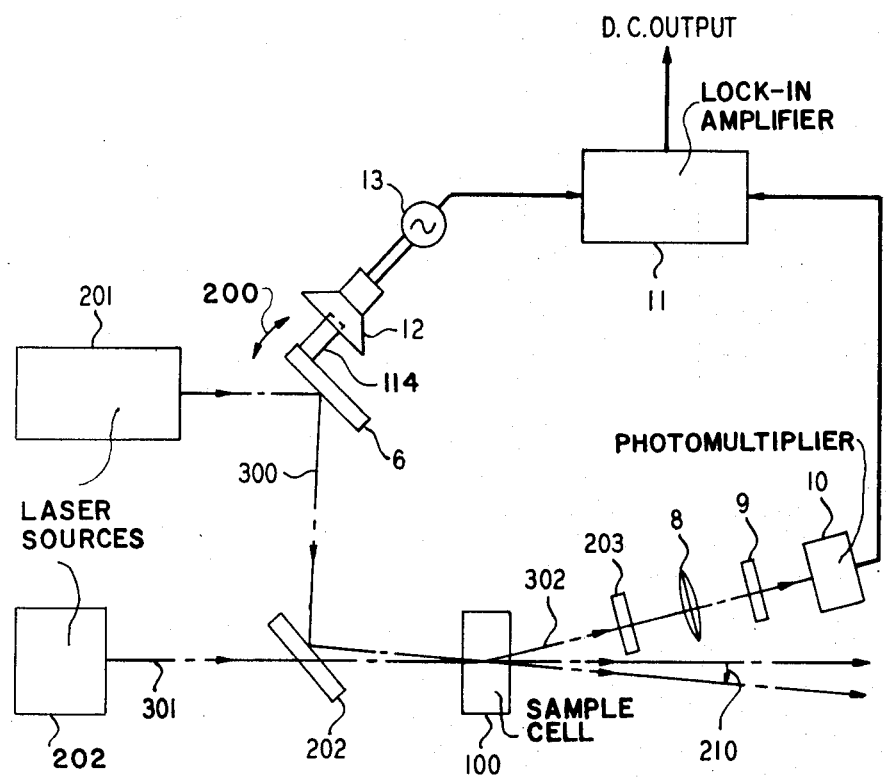
FIG. 3 shows a diagram of an embodiment of the present invention using a coherent anti-Stokes Raman scattering nonlinear mechanism.

Note that the technique of modulation of the direction of an input beam involved in a nonlinear process will produce a modulation of the output beam in response to the changing phasematching conditions. Thus, it should be clear to those skilled in the art that the modulation technique described hereinabove is applicable for use with nonlinear processes other than degenerate four-wave mixing. For example, it would be useful in coherent-anti-Stokes-Raman scattering (CARS). In this scattering the frequencies of the photons used are given by $$\omega_1 - \omega_2 + \omega_3 \rightarrow \omega\text{output} \quad (1)$$

where $\omega_1 - \omega_2$ is equal to the frequency of the Raman transition and $\omega_1 = \omega_3$. FIG. 3 shows an example of an apparatus designed according to the present invention for CARS spectroscopy.

Lasers 202 and 201 provide photons at frequencies $\omega_1$ and $\omega_2$. As described hereinabove, mirror 6 is angle modulated by rod 114, which is affixed to speaker 12. Speaker 12 is driven by voltage source 13. Beam 300 from laser source 201 has its direction modulated by mirror 6. Beam 301 passes through beam splitter 202 to impinge upon sample call 100. Beam 300 is directed by beam spitter 202 to impinge upon sample cell 100 at angle 210 with respect to beam 301. Angle 210 is chosen to satisfy the phasematching condition for CARS. This ange is also useful in preventing beams 300 and 301 form entering the detection apparatus. The outputput beam 302 from cell 100 is passed through filter 203, lens 8, pinhole 9 and is detected by detector 10. The output of detector 10 is fed into lock-in amplifier 11 where that part which is synchronous with the signal from voltage source 13 is converted to d.c. level.

I claim:

1. Apparatus for sensitive nonlinear optical spectroscopic analysis of a sample which comprises:
    means (1, 3) for generating at least two beams of radiation;
    means (4, 6) for guiding said at least two beams of radiation to impinge upon said sample along a plurality of predetermined directions;
    detector means (7, 8, 9, 10) for detecting radiation obtained from said sample after irradiation by said at least two beams of radiation;
    characterized in that
    said apparatus further includes means (12, 13, 14) for modulating at least one of said predetermined directions at a predetermined modulating frequency, and wherein said detector means is sensitive to said modulating frequency.

2. The apparatus as defined in claim 1 wherein said means for generating at least two beams of radiation includes a laser means (1) for generating laser radiation.

3. The apparatus as defined in claim 2 wherein said detector means includes a pinhole (9)

4. The apparatus is defined in claim 3 wherein said means for guiding said at least two beams of radiation includes a mirror (6).

5. The apparatus as defined in claim 4 wherein said means for modulating includes means (12, 13, 14) for modulating the tilt of said mirror.

6. A method for sensitive nonlinear optical spectroscopic analysis of a sample which comprises the steps of:
    generating at least two beams of radiation;
    guiding said at least two beams of radiation to impinge upon said sample along a plurality of predetermined directions;
    detecting radiation obtained from said sample after irradiation by said at least two beams of radiation;
    characterized in that
    said step of guiding includes modulating at least one of said predetermined directions at a predetermined modulating frequency.

7. Apparatus for sensitive four-wave degenerate mixing analysis of the sample contained in a cell (100) which comprises:
    a tunable source (1) for generating a first beam of laser radiation;
    splitter means (3), disposed in the path of said first beam, for splitting said first beam into a second beam and a third beam, said second beam being directed to impinge upon said cell along a first direction;
    director means (4), disposed in the path of said third beam, for directing said third beam to impinge upon said cell along a second direction;
    reflector means (6), disposed after said cell in the path of said second beam, for providing a counterpropagating beam from said second beam, whereby a conjugate beam is produced when said second beam, said third beam and said counterpropagating beam inpinge upon said cell, said conjugate beam counterpropagating along said second direction;
    separator means (7), disposed in the path of said conjugate beam, for separating said conjugate beam from said third beam; and
    detection means (8, 9, 10) for detecting said conjugate beam and producing a signal responsive thereto;
    characterized in that
    said apparatus further includes means (12, 13, 14) for modulating the orientation of said reflector means at a predetermined modulating frequency, whereby the direction of said counterpropagating beam is modulated; and lock-in means (11) for producing an output signal from said signal which is sensitive to said predetermined modulating frequency.

8. Apparatus for sensitive coherent anti-Stoke-Raman scattering analysis of a sample contained in a cell (100) which comprises;

a first tunable source (201) for generating a first beam of laser radiation;

a second source (202) for generating a second beam of laser radiation;

first reflector means (6) disposed in the path of said first beam, for directing said first beam into a first direction;

director means (202) disposed in the path of said first beam and said second beam, for directing said first beam to impinge upon said cell from a second direction and for directing said second beam to impinge upon said cell from a third direction, whereby anti-Stokes Raman scattered radiation is produced; and detection means (203, 8, 9, 10) for detecting said anti-Stokes Raman scattered radiation and producing a signal responsive thereto;

characterized in that said apparatus further includes means (12, 13, 14) for modulating the orientation of said first reflector means at a predetermined modulating frequency, whereby said second direction is modulated; and lock-in means for producing an output signal from said signal which is sensitive to said predetermined modulating frequency.

* * * * *